US008501427B2

(12) United States Patent
Morgan et al.

(10) Patent No.: US 8,501,427 B2
(45) Date of Patent: Aug. 6, 2013

(54) FACTOR H POLYMORPHISMS IN THE DIAGNOSIS AND THERAPY OF INFLAMMATORY DISEASES SUCH AS AGE-RELATED MACULAR DEGENERATION

(75) Inventors: Bryan Paul Morgan, Cardiff (GB); Claire Louise Harris, Cardiff (GB); Svellana Hakobyan, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 665 days.

(21) Appl. No.: 12/524,196

(22) PCT Filed: Jan. 23, 2008

(86) PCT No.: PCT/GB2008/000218
§ 371 (c)(1),
(2), (4) Date: Jul. 23, 2009

(87) PCT Pub. No.: WO2008/090332
PCT Pub. Date: Jul. 31, 2008

(65) Prior Publication Data
US 2010/0009393 A1    Jan. 14, 2010

(30) Foreign Application Priority Data

Jan. 23, 2007    (GB) .................................. 0701213.1

(51) Int. Cl.
| | |
|---|---|
| *A61K 39/395* | (2006.01) |
| *C07K 16/28* | (2006.01) |
| *C12N 5/20* | (2006.01) |
| *G01N 33/53* | (2006.01) |
| *G01N 33/535* | (2006.01) |
| *G01N 33/536* | (2006.01) |
| *G01N 33/543* | (2006.01) |
| *G01N 33/563* | (2006.01) |
| *G01N 33/577* | (2006.01) |
| *C12P 21/08* | (2006.01) |

(52) U.S. Cl.
USPC .................... 435/7.92; 424/139.1; 424/152.1; 424/158.1; 435/7.1; 435/7.21; 435/7.93; 435/7.94; 435/7.95; 435/70.21; 435/452; 435/331; 435/334; 435/337; 435/962; 435/975; 436/512; 436/518; 436/536; 436/548; 436/164; 436/172; 436/811; 436/821; 530/387.9; 530/388.22; 530/388.25; 530/389.3; 530/391.1; 530/391.3; 530/806

(58) Field of Classification Search
USPC ............... 435/7.1, 7.21, 7.8, 7.92, 7.93, 7.94, 435/7.95, 69.7, 70.21, 452, 331, 334, 337, 435/962, 975; 436/518, 536, 547, 548, 164, 436/172, 811, 821, 512; 530/300, 350, 380, 530/387.9, 388.22, 388.25, 389.3, 391.1, 530/391.3, 403, 806, 830; 424/139.1, 141.1, 424/152.1, 158.1, 172.1

See application file for complete search history.

(56) References Cited

U.S. PATENT DOCUMENTS

2007/0037183 A1 * 2/2007 Edwards et al. .................. 435/6

FOREIGN PATENT DOCUMENTS

| WO | WO 2006/062716 | 6/2006 |
| WO | WO 2006/088950 | 8/2006 |
| WO | WO 2007/118095 | 10/2007 |

OTHER PUBLICATIONS

Ripoche et al., 1988b. Two populations of complement factor H differ in their ability to bind cell surfaces. Biochemical Journal 253: 475-480.*
Day et al., 1988. Sequence polymorphism of human complement factor H. Immunogenetics 27: 211-214.*
Schulz et al., 1984. Use of monoclonal antibodies against factor H to investigate the role of a membrane-associated protein antigenically related to H in C3b-receptor function. Journal of Immunology 132: 392-398.*
Harris et al., 2002. Efficient generation of monoclonal antibodies for specific protein domains using recombinant immunoglobulin fusion proteins: pitfalls and solutions. Journal of Immunological Methods 268: 245-258.*
Blackmore et al., 1996. Identification of a heparin binding domain in the seventh short consensus repeat of complement factor H. Journal of Immunology 157: 5422-5427.*
Giannakis et al., 2003. A common site within factor H SCR 7 responsible for binding heparin, C-reactive protein and streptococcal M protein. European Journal of Immunology 33: 962-969.*
Ripoche et al., 1988a. The complete amino acid sequence of human complement factor H. Biochemical Journal 249: 593-602.*
Rodriguez de Córdoba et al., 2004. The human complement factor H: functional roles, genetic variations and disease associations. Molecular Immunology 41: 355-367.*
Sleister et al., 2002. Subtractive immunization: a tool for the generation of discriminatory antibodies to proteins of similar sequence. Journal of Immunological Methods 261: 213-220.*
Jokiranta T Sakari et al: "Analysis of the recognition mechanism of the alternative pathway of complement by monoclonal anti-factor H antibodies: Evidence for multiple interactions between H and surface bound C3b" 1996, FEBS Letters, vol. 393, NR. 2-3, pp. 297-302, xp002490069, ISSN: 0014-5793.
Hakobyan et al: "A novel monoclonal antibody specific for the 402His variant of complement factor H enables identification of the Tyr402His polymorphic status in serum samples" Molecular Immunology, Elmsford, NY, US, vol. 44, No. 16, Sep. 1, 2007, p. 3951, XP022227664, ISSN: 0161-5890.
Hakobyan et al.: "Measurement of factor H variants in plasma using variant-specific monoclonal antibodies: Application to assessing risk of age-related macular degeneration" Investigative Opthamology and Visual Science, vol. 49, No. 5, May 2008, pp. 1983-1990, XP009104031.
Vicky M. Avery, et al., "Characterization of Factor H Binding to Human Polymorphonuclear Leukocytes", The Journal of Immunology, vol. 151, No. 10, pp. 5545-5553; Nov. 15, 1993.
"Microheterogeneity of Human Complement Factor H Observed by Hydrophobic Interaction Chromatography is due to a Post-translational Event: Possible Involvement of Tyrosine Sulfation," XIVth International Complement Workshop, Sep. 15-20, 1991, Cambridge, UK, pp. 181-182, P.J. Lachmann et al. Eds.

* cited by examiner

*Primary Examiner* — Mark Shibuya
*Assistant Examiner* — James L Grun
(74) *Attorney, Agent, or Firm* — King & Schickli, PLLC

(57) ABSTRACT

The invention relates to antibodies, including monoclonal and polyclonal, or fragments thereof, which discriminate between the histidine and tyrosine isoforms of Complement Factor H and to their use in diagnostic methods and therapeutic treatments relating to Complement Factor H mediated diseases.

20 Claims, 9 Drawing Sheets

SNP rs1061170

CFH gene
exon 9
1277T>C
tyrosine-to-histidine change (Y402H)

amino acid sequence: | YLENGYNQNYG |   →   | YLENGYNQNHG |
nucleotide sequence: | AATCAAAATTAT |       | AATCAAAATCAT |

FIGURE 4

FACTOR H POLYMORPHISMS IN THE DIAGNOSIS AND THERAPY OF INFLAMMATORY DISEASES SUCH AS AGE-RELATED MACULAR DEGENERATION

The invention relates to a diagnostic method for determining the existence of a risk factor for complement mediated diseases including, but not limited to, Age-Related Macular Degeneration (AMD); a kit therefor and component parts thereof and, in particular, antibodies used in the aforementioned methodology and kit.

Age-Related Macular Degeneration is a common cause of blindness and its incidence, in the western world and in particular North America and Europe, is increasing, partly, due to the advancing age of the population (1). It therefore follows that the significance of this disease in terms of healthcare costs and quality of life for affected individuals is likely to increase over the coming years.

The disease is characterised by the appearance of retinal deposits, called drusen, which are thought to form a barrier between the retinal pigment epithelium and the choroidal circulation. The deposits lead to the growth of new blood vessels from the choroid into the retina. These new vessels tend to be delicate and can leak or bleed. This symptom gives rise to the "wet" form of Age-Related Macular Degeneration and causes disciform degeneration which leads to distortion of image and rapid loss of vision. However, even if this does not occur, areas of the retina may atrophy, possibly due to anoxia. This latter symptom is known as the "dry" form of the disease, also known as geographic atrophy.

As will be appreciated, late manifestations of the disease result in the inability to read and to perform daily tasks. There is therefore an urgent need for the early diagnosis of the condition and so the early use of prophylactic or therapeutic measures to prevent irreversible loss of central vision.

There are a number of types of treatment for the disease including intravitreal injection of anti-VEGF as well as corticosteroids. Other forms of treatment include laser therapy and surgical treatment such as translocation of the retina and photodynamic therapy.

It has been shown that a variant in the Complement Factor H (CFH) gene, increases the risk of AMD (2). This variant is a polymorphism which results due to the substitution of T to C nucleotide at position 1277 in exon 9; one form of CFH has the amino acid histidine at position 402 (H402) and the other variant has a tyrosine (Y402). It is the histidine form that associates with AMD and other inflammatory diseases. For example, the same risk factor (CFH H402) is associated with other pathologies in which complement is implicated, including myocardial infarction (3). Whilst the association of this Y402H risk factor with disease is significant in AMD, diagnosing this risk in concurrence with other risk factors (such as H402 in addition to elevated levels of CRP) is thought to be of particular importance.

CFH has an important part to play in controlling the Complement system.

The complement system is an important defense against pathogens. On activation, the complement system drives inflammation, activates immune cells and directly kills invaders. This powerful pro-inflammatory system carries the potential to cause harm to self when activated to an inappropriate degree or at an inappropriate site. In order to restrict this tendency to harm self, complement is tightly controlled by a battery of regulatory proteins present both in plasma and on cell membranes. Complement Factor H is a fluid-phase complement regulator, present in plasma at 0.2-0.5 g/l, it plays a key role in regulating the complement system, specifically the amplification loop of the alternative pathway. In the few individuals with inherited deficiency of Complement Factor H, the complement system undergoes uncontrolled activation, consuming the complement proteins and rendering the individual deficient in complement (and hence susceptible to infections) (4). More subtle changes in Complement Factor H have recently also been linked with human disease. Mutations clustered in the carboxy-terminal domain of the protein have been linked with atypical haemolytic uraemic syndrome and, as mentioned, a common polymorphism that causes a single amino acid substitution in the middle of the molecule at position 402 is strongly associated with Age-Related Macular Degeneration (AMD) (5). Individuals homozygous for histidine at position 402, approximately 10% of the caucasian population, have a 6-7 fold increase risk of developing AMD compared to those homozygous for tyrosine at this position (2, 5). 50% of the caucasian population are heterozygous for the two alleles, H402 and Y402, these individuals have an approximate 3-fold increase risk. The precise reason why this small change in the large factor H molecule so profoundly alters the risk of AMD is unclear, although evidence is accumulating that the two forms differ in their capacity to attach to cells and tissues (6).

Knowing the Complement Factor H polymorphic status of an individual at risk of AMD (essentially, all elderly people) and other complement mediated diseases would be useful both in predicting risk and in guiding interventions or behaviour modifications to reduce risk. For example, smoking and obesity are independently associated with increased risk of AMD and in H402 homozygotes strenuous efforts could be made to eliminate these modifiable factors. Currently, the only way to discover the Complement Factor H polymorphic status of an individual is to sequence the gene. This involves obtaining fresh blood, extracting DNA from cells and sequencing the relevant region of the gene encoding Complement Factor H, methods that are tedious, time-consuming and only possible in a specialist laboratory. A simple blood test that reliably identified the factor H polymorphic status would enable the rapid screening of the elderly in primary care or eye clinics.

Complement Factor H consists of 1213 amino acids arranged in 20 homologous units, each about 60 amino acids long. The 60 amino acid long repeat units are homologous with those found in a large number of other complement and non-complement proteins. Given that the two polymorphic variants differ by only a single amino acid out of the 1213 residues in the protein, it was not obvious that antibodies could be generated that distinguished the two variant forms of CFH.

However, using selective screening methods, we have been able to produce an antibody that is specific for the H402 variant and a further antibody that is specific for the Y402 variant, each one, or both, of these antibodies enables the production of a reliable and repeatable diagnostic assay from samples of plasma for determining individuals at risk of complement mediated diseases such as AMD.

STATEMENTS OF INVENTION

According to a first aspect of the invention there is therefore provided a method for determining the existence of a risk factor for a complement mediated disease in an individual comprising:
a) obtaining a plasma sample from an individual to be tested;
b) exposing said sample to at least one antibody, or fragment thereof, described herein and specific for either the histidine or tyrosine 402 variant of Complement Factor H;

c) determining specific binding of said antibody to plasma Complement Factor H and where binding of the histidine specific antibody takes place concluding that the histidine 402 variant is present, or where binding of the tyrosine specific antibody takes place concluding that the tyrosine 402 variant is present; and d) where the histidine 402 variant is present, concluding that the individual either has, or is at increased risk of developing, a complement mediated disease, or where the binding of the tyrosine specific antibody indicates a homozygous state for the tyrosine variant concluding that the individual is at reduced risk of developing a complement mediated disease.

In a preferred method of the invention step b) involves the use of monoclonal antibody or a fragment thereof, and preferably, a monoclonal or a fragment thereof specific for the histidine 402 variant or a monoclonal or a fragment thereof specific for the tyrosine 402 variant of the protein. However, ideally, the two monoclonal antibodies, or fragments thereof, are used whereby binding of the two antibodies can be compared and where both the histidine and tyrosine specific antibodies are used and binding of the histidine specific antibody takes place concluding that the individual has, or is at risk of, developing a complement mediated disease.

Reference herein to an antibody fragment includes reference to at least the Complementarity Determining Region(s) of said antibody.

In a preferred method of the invention where step b) involves the use of just the antibody, or a fragment thereof, specific for the tyrosine 402 variant a quantitative assay is undertaken, preferably as described herein, to determine whether the individual is homozygous for the tyrosine variant.

In a preferred method of the invention the disease is Age-Related Macular Degeneration.

In a preferred method of the invention plasma is exposed to said antibody, or a fragment thereof, and followed by a procedure which removes unbound antibodies so that the subsequent determination of binding can be undertaken without, or with a minimum amount of, background interference from unbound antibodies.

In an alternative method of the invention plasma is exposed to solid phase (plate) coated with antibody or antibody fragment (polyclonal or monoclonal) that recognises both variants of factor H, any unbound plasma proteins are washed away before the plate is incubated with antibody or antibody fragment specific for His402 variant or Tyr 402 variant. In this way unbound plasma proteins are removed so that a subsequent determination of binding can be undertaken without, or with the minimum amount of, background interference from unbound proteins.

In both of the above methods the subsequent determination of binding involves either a secondary antibody that binds the isoform-specific monoclonal or the isoform specific antibodies are directly, or indirectly, linked to a labelling system such as an enzyme that catalyses colour development.

Thus, in yet a further preferred embodiment of the invention exposing said plasma to antibody (which may be called primary antibody) is further followed by the use of (what may be called) secondary antibody which binds either the H402 or Y402 specific monoclonal antibody or a fragment thereof. Additionally, preferably, this secondary antibody is coupled to an indicator or labelling system which produces a measure of the binding of, either or both, the primary or secondary antibody to its target and so produces a measure of the binding of the variant-specific antibody to Complement Factor H in the plasma of the individual to be tested.

Most suitably, indicator or labelling systems include, but are not limited to, conventional ELISA systems or bioluminescent, chemiluminescent or pigmented indicator systems.

Preferred assays for determining the binding of antibody to CFH are immunoassay based and include, but are not limited to, any one or more of the following known exemplifications.

1. Standard ELISA.
2. Nephelometric/turbidity assays, where antibody is added to the plasma to bind to CFH. The monoclonal can be triggered to cause turbidity by chemical modification or by adding a crosslinking antibody.
3. Bead-based fluorescent assays (at use in clinical labs for measuring cytokines for example.) Beads are coated with an antibody that recognises both forms of factor H. Added to plasma sample are variant-specific antibodies that have been fluorescently labelled (different colours), this plasma sample is exposed to beads which are then analysed using flow cytometer-based equipment. Colour detected indicates which factor H variants are there.
4. 'Dipstick'. For example, sticks have three spots: one with anti-H402, one with anti-Y402 and one with antibody that recognises both forms (this spot is a control). The stick is dipped into plasma, CFH binds to the relevant spot. The presence of factor H is detected using a second antibody attached to chromophore (could be polyclonal) that sees CFH (any isoform). On developing if H402 spot and control develop—Homozygous H402, Y402 and control=homozygous Y402, all three spots=heterozygous See FIG. 5 where this technology is illustrated.

In preferred methods of the invention, using the above immunoassays, two kinds of assay can be developed:

1. A quantitative ELISA that measures the total CFH and the amount of His402. This assay requires a generic monoclonal that sees any isoform of CFH and, a His-specific monoclonal and, ideally, a polyclonal CFH antibody to capture the CFH in the plasma in order to isolate it for quantification.
2. A quantitative assay which detects the presence of only the His form, or only the Tyr form, or the presence of both forms. Similar to that in FIG. 3, it could also be an ELISA. This assay requires two specific monoclonals and a polyclonal (or non-specific monoclonal) antibody to capture the CFH in the plasma in order to isolate it for identification.

According to a further aspect of the invention there is provided a kit for carrying out the aforementioned methodology which kit comprises an antibody or fragment thereof specific for the histidine 402 variant and/or the tyrosine 402 variant of Complement Factor H, as described herein. Ideally this antibody is monoclonal.

In a preferred kit of the invention the kit also includes an antibody or fragment thereof that recognises any isoform of CFH, such as a monoclonal or polyclonal antibody to CFH.

More preferably still, the kit further includes indicator or labelling means that enables the binding of said one or more antibodies to Complement Factor H in plasma to be determined. It therefore includes, in one option, a secondary antibody which is coupled to an ELISA assay or a light activated or pigment dependent assay. The secondary antibody is specific for the said one or more antibodies to CFH such as the variant-specific antibodies, of the invention.

According to a further aspect of the invention there is provided an antibody, or fragment thereof, that is specific for the H402 variant of Complement Factor H.

According to a further aspect of the invention there is provided an antibody, or fragment thereof, which reacts with the histidine 402 variant of Complement Factor H but does not react with the tyrosine 402 variant of Complement Factor H.

According to a further aspect of the invention there is provided a monoclonal antibody, or fragment thereof, that is specific for the histidine 402 variant of Complement Factor H characterised by any one or more of the above properties and/or the following accession number A 07042601 (ECACC).

According to a yet further aspect of the invention there is provided a monoclonal antibody, or fragment thereof, which specifically recognises and binds the histidine 402 variant of Complement Factor H.

According to a further aspect of the invention there is provided an antibody, or fragment thereof, that is specific for the Y402 variant of Complement Factor H.

According to a further aspect of the invention there is provided an antibody, or fragment thereof, which reacts with the tyrosine 402 variant of Complement Factor H but does not react with the histidine 402 variant of Complement Factor H.

According to a further aspect of the invention there is provided a monoclonal antibody, or fragment thereof, that is specific for the tyrosine 402 variant of Complement Factor H characterised by any one of more of the above properties and/or the following accession number A 08011002 (ECACC).

According to a yet further aspect of the invention there is provided a monoclonal antibody, or fragment thereof, which specifically recognises and binds the tyrosine 402 wild type of Complement Factor H and/or the following accession number A 08011003 (ECACC).

According to a further aspect of the invention there is provided an antibody, or fragment thereof, that recognises either isoform of Complement Factor H.

In a preferred aspect of the invention this isoform recognising antibody is either monoclonal or polyclonal and in the instance where the antibody is polyclonal, ideally, it is an affinity purified polyclonal antibody to Complement Factor H.

According to a further aspect of the invention there is provided a monoclonal antibody, or fragment thereof, prepared by a method comprising the following steps:
a) immunising a non-human mammalian animal with at least one fragment of Complement Factor H which fragment(s) includes either, or both, the histidine 402 variant or the tyrosine 402 variant;
b) taking out at least a part of the spleen of the animal and recovering immune spleen cells;
c) fusing the immune spleen cells with myeloma cells and recovering the fused hybrid cells;
d) cloning the cells by limiting dilution to generate clones of cells each secreting a selected antibody
e) culturing the cloned hybrid cells under conditions that give rise to the production of monoclonal antibody; and
f) recovering monoclonal antibody from the culture.

In a preferred method of the invention said non-human animal is immunised with a fusion protein comprising said histidine 402 variant fragment of Complement Factor H and a Fc portion of human IgG4. More preferably still, said non-human animal is immunised with an additional, or alternative, fragment of Complement Factor H which comprises a tyrosine 402 wild type fragment, produced as a fusion protein and so coupled to a Fc portion of human IgG4.

As those skilled in the art will appreciate, when practising the method of the invention immunising an animal with said first of the above fusion proteins will result in, amongst other things, the production of monoclonal antibodies specific for the histidine 402 variant and, similarly, immunising said animal with the second of the above described fusion proteins will result in, amongst other things, the production of monoclonal antibodies specific for the tyrosine 402 variant of CFH. However, additionally, monoclonal antibodies will also be produced that recognise other shared epitopes of the two immunising proteins and so, using this technique, it is possible to obtain three types of monoclonal antibody: histidine 402 specific; tyrosine 402 specific and monoclonal that will recognise either form of CFH.

Most preferably still said non-human animal is immunised with both of the aforementioned fusion proteins and so, at the end of the procedure, monoclonal antibodies to either of the native Complement Factor H variants, either H402 or Y402, are obtained.

In a preferred method of the invention step d) is followed by a screening process which screens the clones of cells in order to identify those producing specific monoclonal antibodies against the factor H variants.

According to a further aspect of the invention there is provided a clone that secretes one or more of the aforesaid antibodies or fragments thereof.

According to a further aspect of the invention there is provided a polyclonal antibody that recognises either isoform of Complement Factor H prepared by a method comprising the following steps:
a) immunising a non-human mammalian animal with Complement Factor H or a fragment thereof;
b) extracting plasma from said animal;
c) fractionating the plasma in order to extract antibody specific for Complement Factor H.

According to a further aspect of the invention there is provided use of a monoclonal antibody, or a fragment thereof, specific for either the histidine or tyrosine 402 variant version of Complement Factor H for inhibiting the binding of Complement Factor H to either ligands or tissues.

According to a further aspect of the invention there is provided a therapeutic comprising a monoclonal antibody, or a fragment thereof, specific for either the histidine or tyrosine 402 variant of Complement Factor H.

In a preferred aspect of the invention this therapeutic is useful in overcoming complement mediated diseases by preventing the participation of Complement Factor H in inflammatory conditions mediated by complement.

According to a further aspect of the invention there is provided the diagnostic use of a monoclonal antibody, or a fragment thereof, specific for either the histidine or tyrosine 402 variant of Complement Factor H.

In this aspect of the invention the antibody is used to detect the presence of a specific isoform of Complement Factor H in tissue, for example, it may be used to detect the presence of Complement Factor H in the eye in order to aid assessment of the presence of, or the beginning of, age-related macular degeneration.

According to a further aspect of the invention there is provided a fusion protein as described herein for the production of monoclonal antibody.

According to a yet further aspect of the invention there is provided primers useful for the production of a fusion protein as described herein.

An embodiment of the invention will now be described by way of example only with reference to the accompanying Figures wherein:

FIG. 1a shows a western blot analysis of plasma Complement Factor H (fH). Plasma was electrophoresed on a 7.5% gel as indicated, transferred to nitrocellulose and probed with (a) MBI-7 mAB specific for histidine CFH (HfH) and (b) with a mAb identifying both forms of CFH (fH);

FIG. 1b shows western blot analysis of plasma complement factor H (fH). Plasma from donors (HH402: homozygote for His form, YY402: homozygote for Tyr form, YH402: heterozygote) was electrophoresed on a 7.5% gel as indicated. Proteins were transferred to nitrocellulose and probed with mAb as indicated. OX24 identifies both forms of CFH (fH), MBI-7 is specific for the histidine CFH (HfH);

Figure 2A:
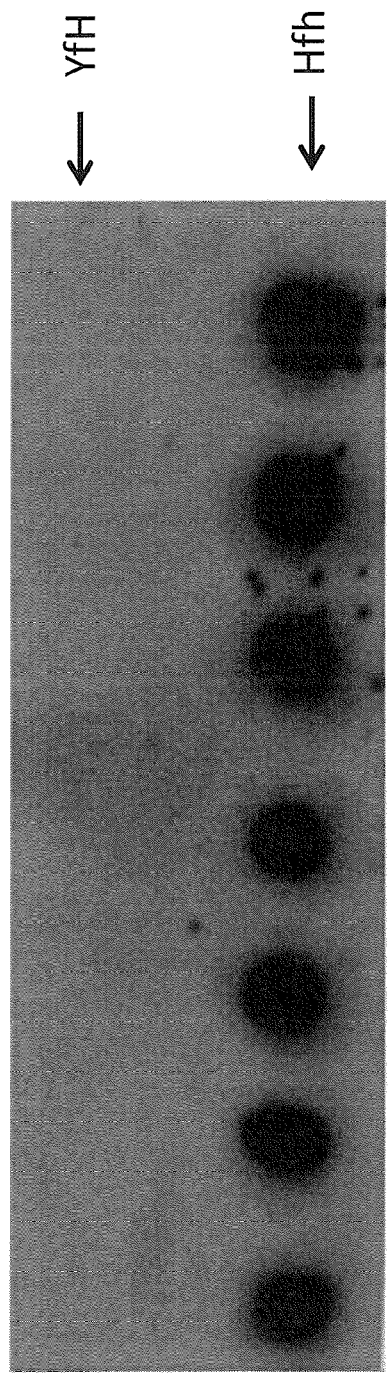
FIG. 2a shows dot blot of endogenous CFH purified from individuals homozygous for either H CFH (HfH) or Y CFH (YfH). MBI-7 mAB identified only H CFH (HfH)
Figure 2B:
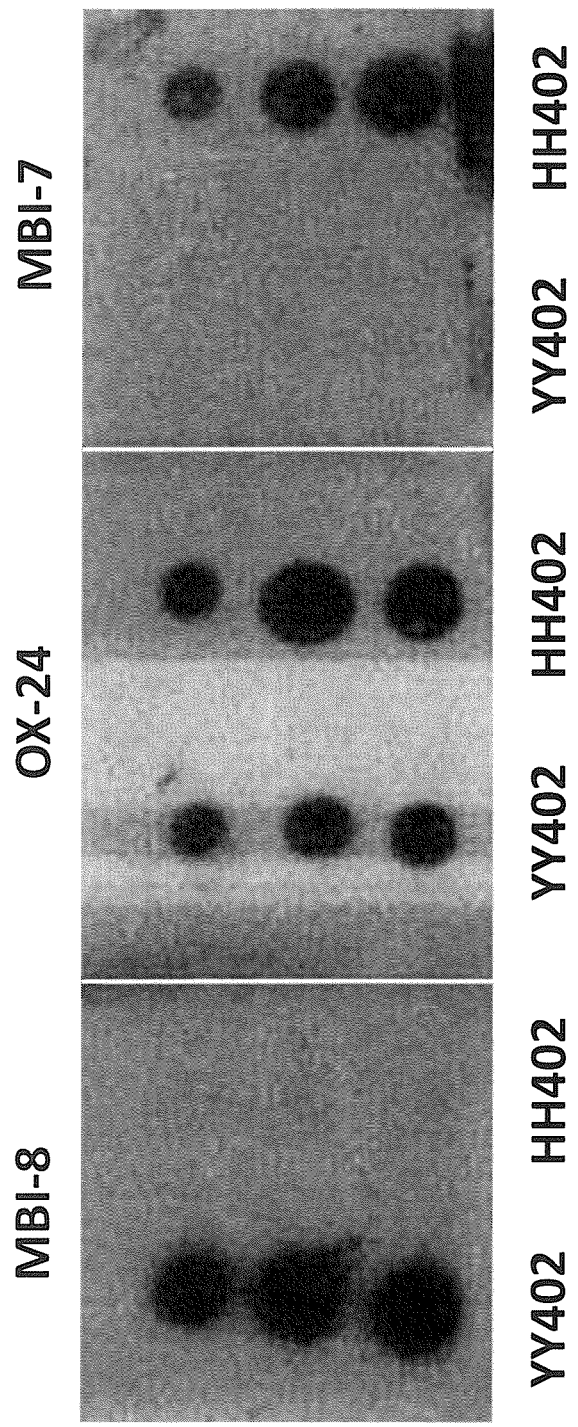
Figure 3A:
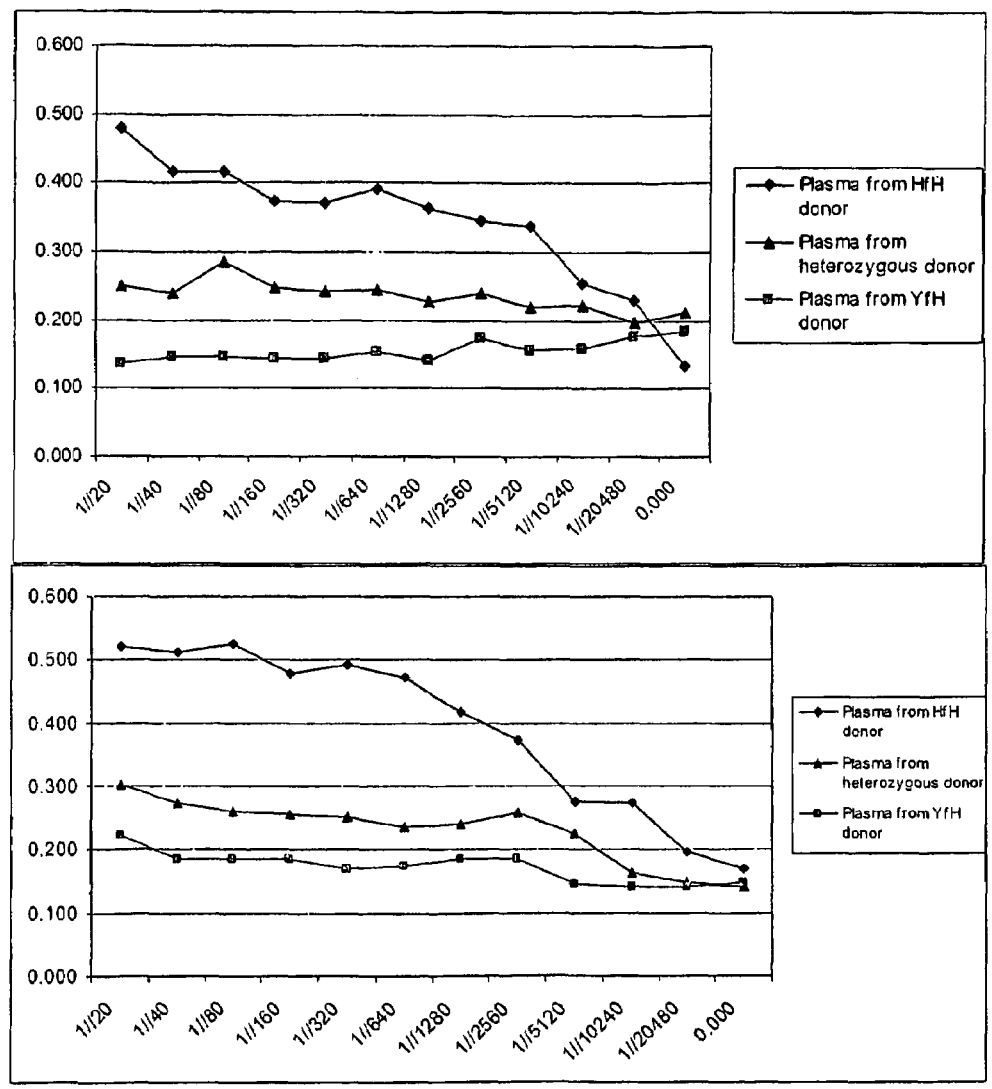
Figure 3B:
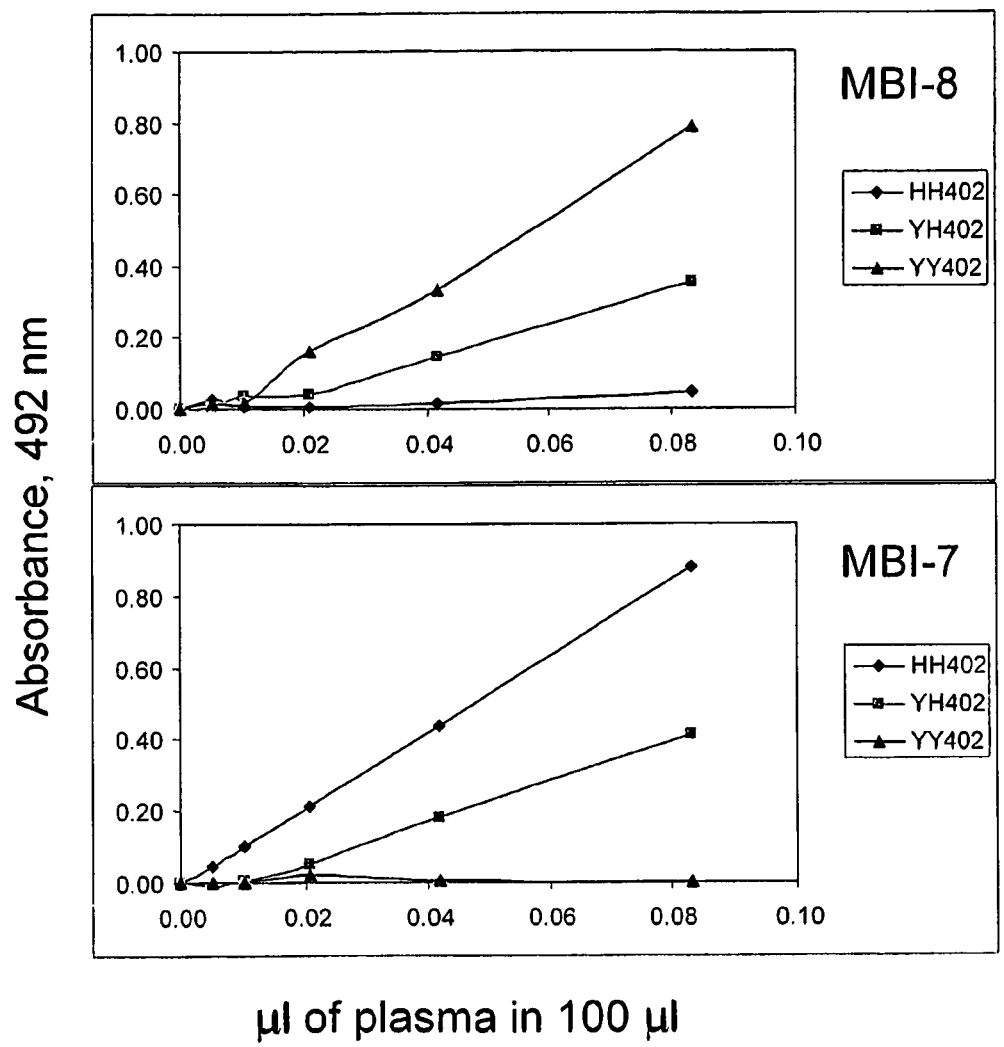
Figure 5A:
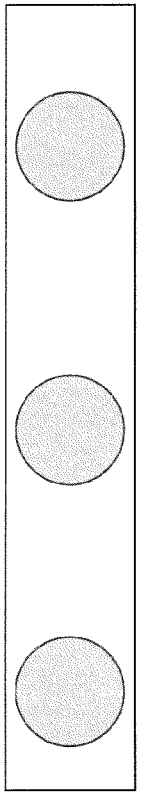
Figure 5A:
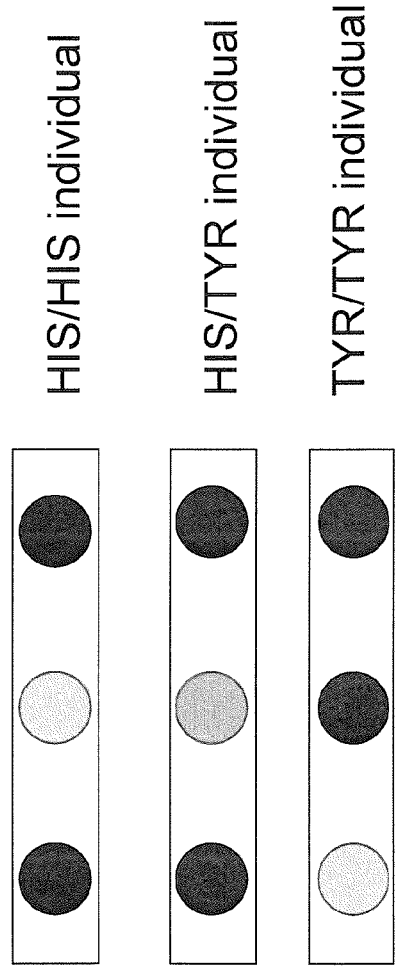
Figure 5B:
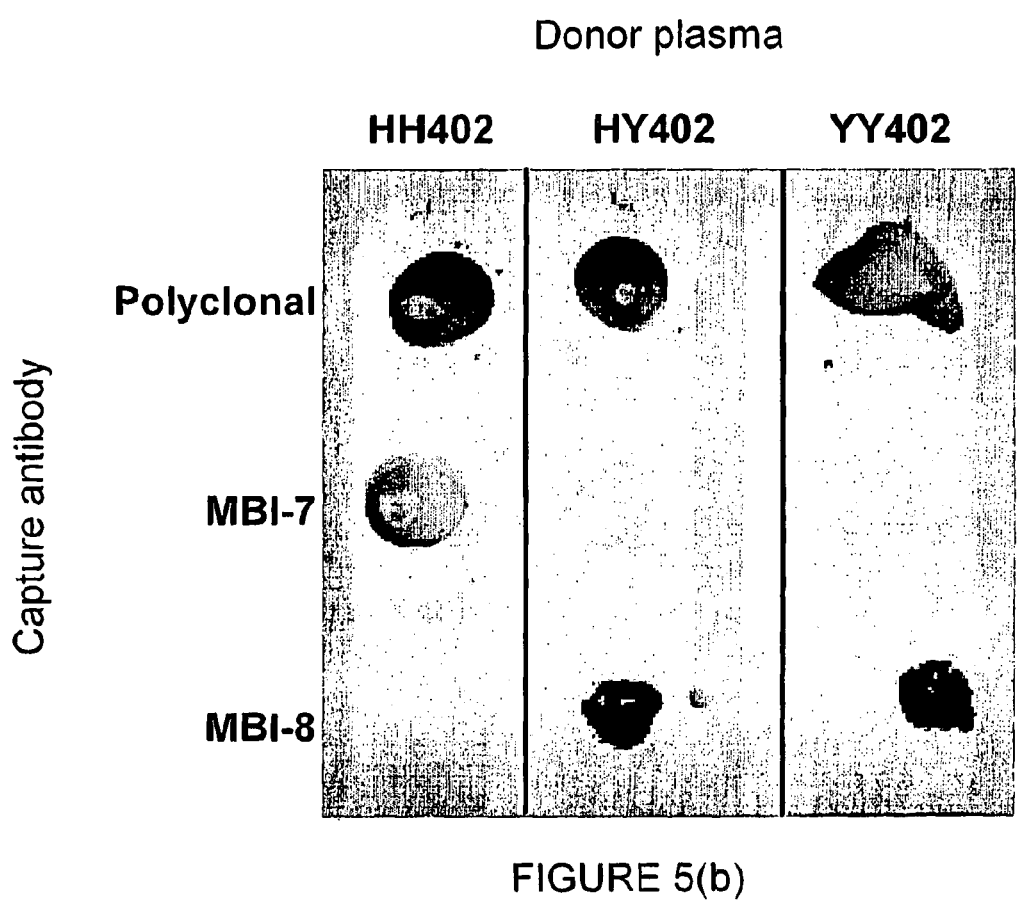

FIG. 2b shows dot blot of endogenous CFH purified from individuals homozygous for either HfH (HH402) or YfH (YY402). Blots were probed with MBI-7, MBI-8 or OX24 (binds both forms). MBI-7 identified only HfH, MBI-8 detected only YfH and OX24 detected both HfH and YfH;

FIG. 3a shows ELISA demonstrating specific detection of CFH in plasma from donors known to be either homozygous H CFH (HfH) or Y CFH (YfH) or heterozygous for the Y402H polymorphism. In the two examples of this assay illustrated in FIG. 3, dilution of plasma is on the x-axis and A490 on the y-axis;

FIG. 3b shows ELISA demonstrating specific detection of CFH in plasma from donors known to be either homozygous HfH (HH402, diamonds), or homozygous YfH (YY402, triangles), or heterozygous for the Y402H polymorphism (YH402, squares). Plates were coated with polyclonal antibody for capture and either MBI-7 or MBI-8 used to detect as indicated. In the two examples of this assay illustrated in FIG. 3, the amount of plasma is indicated on the x-axis (µl plasma in 100 µl buffer final volume) and the A492 on the y-axis;

FIG. 4 shows a fragment of the nucleotide and corresponding amino acid sequence structure of CFH showing T to C substitution at 1277 and H402Y variant, respectively;

FIG. 5a shows a procedure for a dip-stick assay for determining the genotype of Complement Factor H in an individual to be tested; and FIG. 5b shows a dip-stick assay for determining the genotype of CFH in an individual to be tested. In this example, 20 µg of each antibody (polyclonal, MBI-7 and MBI-8 as indicated) were loaded on the membrane. After blocking the membranes were cut into strips, which were then incubated with plasma samples from individuals that were YY402 homozygous, YH402 heterozygous or HH402 homozygous, plasma was diluted (2% plasma v/v) in PBS/milk. After 30 min, strips were washed in PBS/Tween, then incubated with polyclonal antibody directly conjugated to horseradish peroxidase. After 15 mins, strips were washed in PBS/Tween and bound fH was detected using colour development (chloronapthol development).

METHOD STATEMENT

Proteins

The H402Y polymorphism resides in short consensus repeat (SCR) domain 7 of factor H. To target this region, fusion proteins comprising the Fc portion of human IgG4 attached to SCRs 6, 7 and 8 of human factor H were engineered and expressed essentially as described (7).

1. RNA from human PBL was isolated and converted to cDNA by RT-PCR
2. Specific primers were used to amplify DNA encoding SCR6-8.

```
(a) Sense primer:
                                            (SEQ ID NO 1)
    (5') gcgtctagaaccttgaaaccttgtgattatcc (3')

(b) Antisense primer:
                                            (SEQ ID NO 2)
    (5') cagggatccagatttaatgcacgtgggttg (3')
```

These primers contain additional nucleotide sequences to enable digestion by restriction enzymes and ligation into the expression vector.

3. The DNA was ligated into a plasmid downstream and in frame with DNA encoding the signal peptide of CD33. The resulting plasmid was used as template for subsequent PCR where the amplified DNA product included sequence encoding the signal peptide and factor H.

4. Purified DNA encoding the signal peptide and factor H SCRs was ligated into a plasmid upstream of DNA encoding the Fc region of human IgG4. This methodology generated a DNA construct encoding the His variant of CFH.

5. To generate a construct encoding the Tyr form of factor H, new primers were designed that introduced a point mutation into the previously-generated His construct. Two stage PCR was used to generate a new construct containing DNA encoding the Tyr variant of factor H.

```
Primer 1 (used with primer (b) above):
                                            (SEQ ID NO 3)
    (5') aatcaaaattatggaagaaag (3')

Primer 2 (used with primer (a) above):
                                            (SEQ ID NO 4)
    (5') ctttcttccataattttgatt (3')
```

6; DNA encoding the Tyr variant was ligated into the expression vectors as described above in 3 and 4 such that the DNA encoding the Tyr variant was in frame with DNA encoding the CD33 signal peptide and DNA encoding the Fc region of human IgG4.

7. CHO cells were transfected with the vector encoding either construct.

8. Fusion protein was purified from the supernatant of transfected cell lines.

Two fusion proteins were generated, one with H at the relevant position in SCR 7 (HfH-Fc) and one with Y at this position (YfH-Fc). The recombinant fusion proteins were purified to homogeneity on protein A sepharose.

To obtain native factor H of only one isoform, either H402 (HfH) or Y402 (YfH), appropriate donors were identified by genotyping, bled and factor H purified from plasma by affinity chromatography on immobilized anti-factor H antibody. The purified proteins were assessed for purity by SDS-PAGE analysis.

Immunisation Protocols

Balb/C mice were immunised with either the HfH-fC or the YfH-Fc fusion proteins in complete Freund's adjuvant. Four weeks later, mice were boosted with the same protein in incomplete Freund's adjuvant and two further boosts were administered at 3 week intervals. Mice were then test-bled and serum antibody responses tested in ELISA against the two fusion proteins and the H and Y forms of purified factor H. Mice giving strong responses against the relevant fusion proteins and purified factor H were given a final boost without adjuvant. Spleens were then harvested and spleen cells fused with myeloma cells to generate antibody-secreting hybridomas using standard protocols. Fusion mixes were aliquoted into either six 24-well plates or six 96-well plates and placed in a 37° C. incubator. After two weeks, supernatants were harvested and screened by ELISA for antibodies against purified factor H (mix of HfH and YfH). Positive wells were subjected to limiting dilution cloning in 96-well plates. After a further two weeks, supernatants from clone plates were screened by ELISA for antibodies reactive with factor H; two separate screens were performed against HfH and YfH respectively. Cells from wells showing strong reactivity against one variant of factor H but not the other were re-cloned and the process repeated a further two times. Clones remaining specific for one form of factor H at the end of this process were grown in bulk for generation of antibody.

Characterisation of Anti-Factor H Antibodies

Immunoglobulin class and sub-class was tested for each antibody using a commercial isotyping kit. Specificity for HfH over YfH (or vice versa) was tested in ELISA and western blot using HfH and YfH.

Clones secreting the monoclonal antibodies described herein have been deposited at The European Collection of Cell Cultures (ECACC) at Porton Down under the following accession numbers:

Monoclonal specific for the H402 variant of Complement Factor H A 07042601, 26 Apr. 2007 (Clone MB1-7).

Monoclonal antibodies specific for the Y402 variant of Complement Factor H A 08011002, 10 Jan. 2008 (Clone MB1-8).

Monoclonal antibodies specific for either isoform of Complement Factor H A 08011003, 10 Jan. 2008 (Clone MB1-9).

European Collection of Cell Cultures (ECACC)
Health Protection Agency
Centre For Emergency Preparedness and Response
Porton Down, Salisbury, Wiltshire SP4 0JG. UK Development of an ELISA Specifically Detecting HfH in Plasma Samples ELISA plates were coated with polyclonal anti-factor H (commercial or in-house affinity-purified polyclonal anti-factor H) and blocked with BSA. Plasma samples from individuals of known (from genotyping) factor H status (homozygous HfH, homozygous YfH or heterozygous) were diluted in PBS/Tween and incubated in the wells. After washing, the test antibody diluted in PBS/BSA was incubated in the wells. After further washes, plates were finally incubated with a HRP-conjugated anti-mouse immunoglobulin reagent (commercial). Plates were developed using O-phenyldiamine (OPD) and absorbance read in a plate spectrophotometer.

Complementarily Determining Regions

Assays may also use fragments of monoclonal antibodies generated by recombinant technology or by enzymatic digestion.

Single-chain Fv are antigen binding units comprising a single polypeptide chain encoded by one gene. ScFv may also be fused to other protein or peptide domains using recombinant technology. Small, recombinant forms of the antibody are generated by isolating mRNA from the hybridoma (e.g. MBI7, MBI8 . . . ) and generating DNA encoding the variable regions by RT-PCR. DNA encoding the variable regions from the heavy and light chains is cloned into an appropriate expression vector. The expression vector may also encode a leader sequence for expression and a linking domain between the two variable regions (for example, $(GGGGSGGGS)_2$) (SEQ ID NO 5). In some cases, DNA encoding an additional protein domain (or peptide domain) may be cloned in frame with DNA encoding the antibody fragment. Vectors suitable for expression of recombinant protein in eukaryotic or prokaryotic cells are used, in the latter case the recombinant antibody fragments are refolded from inclusion bodies and purified using classical chromatographic techniques.

In some cases DNA encoding the scFv is cloned into a phagemid vector which is transformed into appropriate bacteria. Phage rescue (by infection with helper phages) and subsequent panning of isolated phage on factor H enables isolation of a clone which binds factor H with the desired affinity. Phage rescued from panning can then be used to infect a suitable bacterial strain resulting in soluble scFv.

Monoclonal antibodies may also be fragmented into smaller units for use in assays. Enzymatic digestion with enzymes, for example pepsin or papain, will result in fragments such as $Fab_2$ or Fab which can be purified from the mixture by classical chromatographic techniques.

Results

Characterisation of Antibodies

Figure 1A:
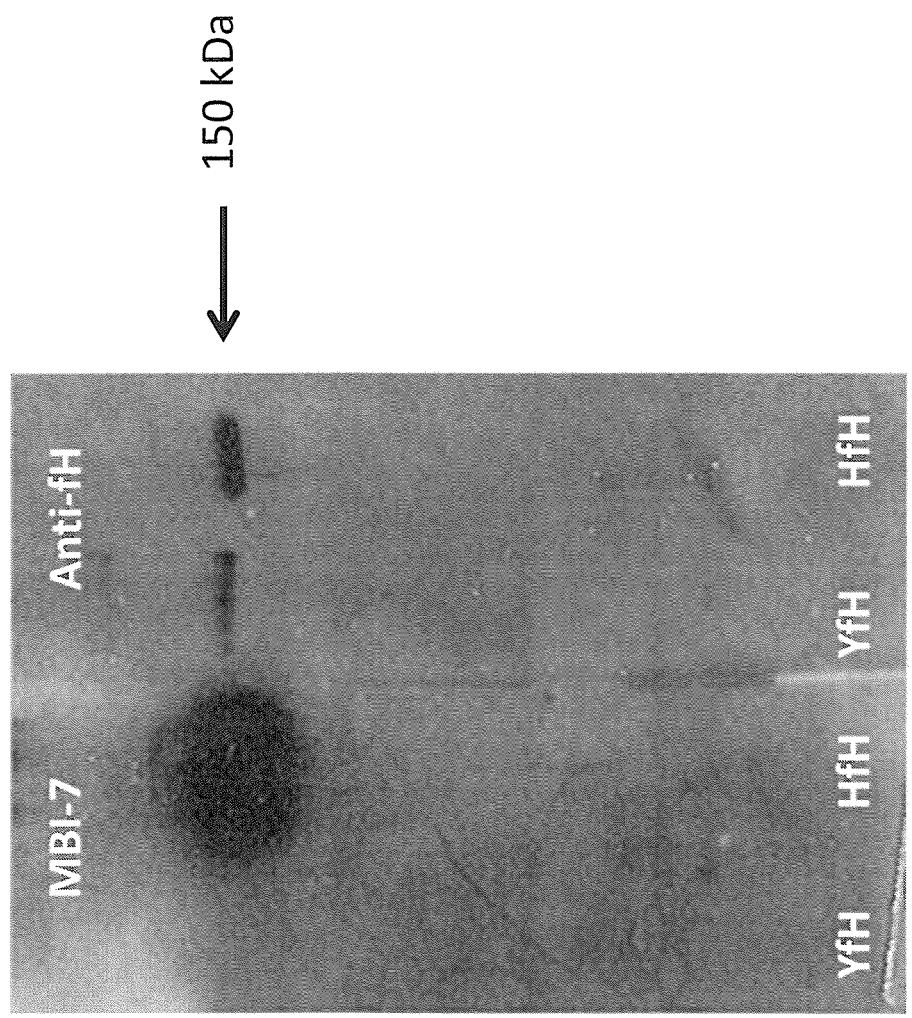
FIG. 1c is a western blot analysis of plasma complement factor H performed as described in FIG. 1a. The mAb used to probe the blot are MBI-7 specific for HfH and MBI-8 specific for the tyrosine CFH (YfH) as indicated.
Figure 1:
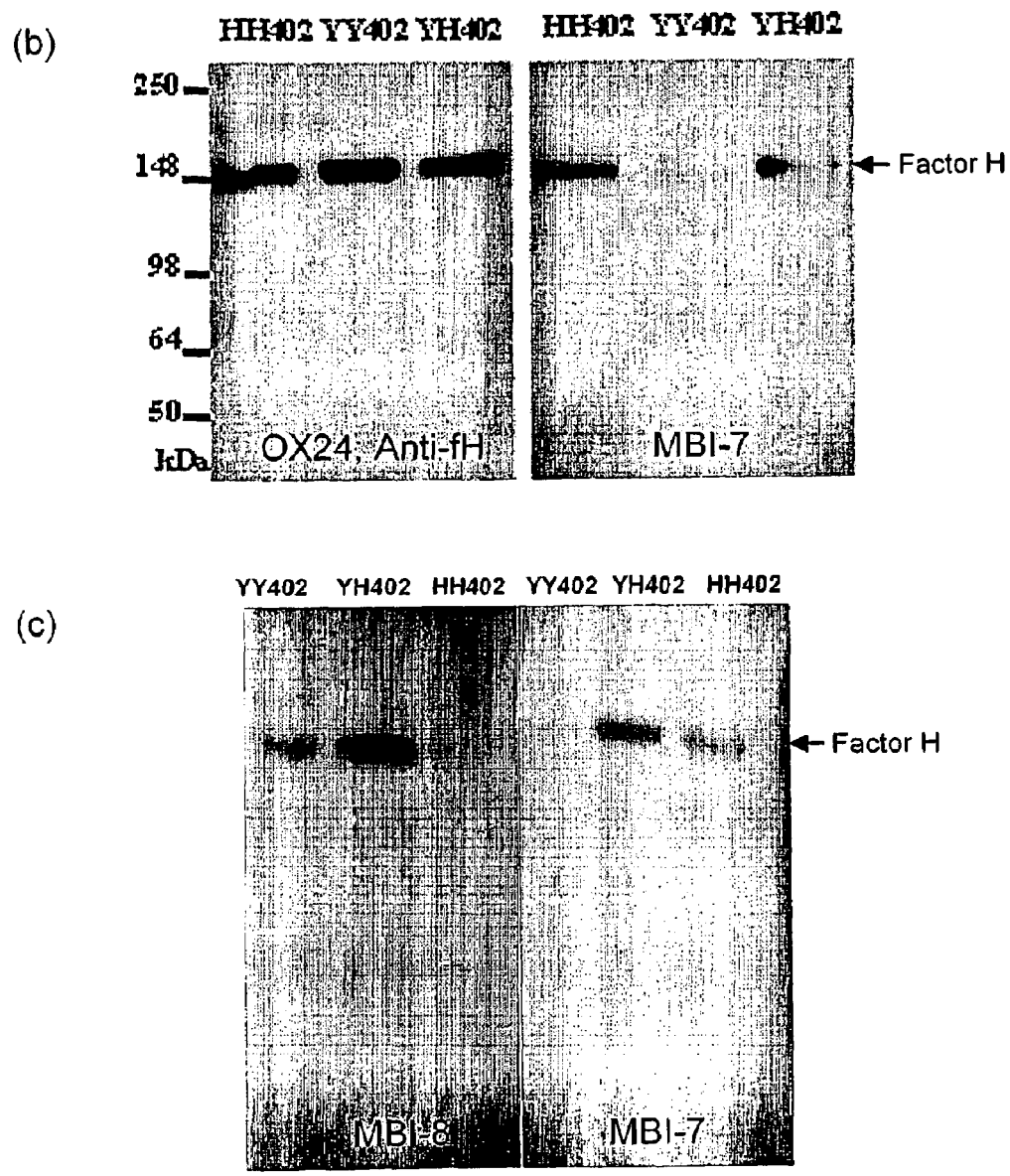

From original cloning plates, many clones were identified that were reactive with purified CFH. Of these, several reacted predominantly or exclusively with HfH or YfH in the second ELISA screen. One of these mAb, termed MBI-7, was tested in western blotting against plasma from donors known to be homozygous either for HfH or YfH or heterozygote donors. The mAb MBI-7 detected a strong band at the correct size for CFH in HfH and heterozygote donors but was completely negative when used to probe plasma from YfH homozygote donors (FIG. 1a). A second antibody, MBI-8, was similarly tested in western blotting against plasma from donors and detected a strong band at the correct size for CFH in YfH and heterozygote donors but was completely negative when used to probe plasma from HfH donors (FIG. 1b). In contrast, CFH was detected in all plasma samples by a monoclonal antibody known to bind both HfH and YfH (FIG. 1a). Both mAb MBI-7 and mAb MBI-8 showed the same specificity to purified HfH in dot blotting (FIG. 2).

Establishment of an ELISA Assay Specific for HfH

In the ELISA using the HfH mAb MBI-7 as detection reagent, plasma from donors known to be homozygous HfH gave a strong displacement across the dilution range tested. In contrast, plasma from YfH homozygotes was essentially negative in the assay. Plasma samples from individuals heterozygous for the polymorphism gave intermediate values and were easily distinguished from either homozygote (FIG. 3).

Demonstration of a Dipstick Assay

An example of a dipstick assay is illustrated where MBI-7, MBI-8 or polyclonal antibody are applied to membrane in distinct spots (FIG. 5). The membrane is used to capture CFH from plasma samples and bound CFH is detected with HRPO-conjugated polyclonal antibody. Colour was developed using chloronapthol. MBI-7 gave a positive signal from HfH homozygote or heterozygote donors whereas MBI-8 gave a positive signal from YfH homozygote or heterozygote donors. Where polyclonal antibody was used as capture, as signal was obtained with all capture antibodies.

Discussion

We describe the generation of two mAb, each specific for one of the two polymorphic variants at residue 402 in factor H. These unique reagents enable the rapid and simple phenotyping of individuals using ELISA. The mAbs also provide a means for detecting the specific deposition of a particular polymorphic variant in tissues in disease and provide a tool to inhibit CFH binding to ligands in tissues.

REFERENCES

1. Gehrs K M, Anderson D H, Johnson L V, Hageman G S. Age-related macular degeneration-emerging pathogenetic and therapeutic concepts. Ann Med. 2006; 38(7): 450-71.

2. Klein R J, Zeiss C, Chew E Y, Tsai J Y, Sackler R S, Haynes C, Henning A K, SanGiovanni J P, Mane S M, Mayne S T, Bracken M B, Ferris F L, Ott J, Barnstable C, Hoh J. Complement factor H polymorphism in age-related macular degeneration. Science. 2005 Apr. 15; 308(5720):385-9.
3. Kardys I, Klaver C C, Despriet D D, Bergen A A, Uitterlinden A G, Hofman A, Oostra B A, Van Duijn C M, de Jong P T, Witteman J C. A common polymorphism in the complement factor H gene is associated with increased risk of myocardial infarction: the Rotterdam Study. J Am Coll Cardiol. 2006 Apr. 18; 47(8):1568-75.
4. Thompson R A, Winterborn M H. Hypocomplementaemia due to a genetic deficiency of beta 1H globulin. Clin Exp Immunol. 1981 October; 46(1):110-9.
5. Haines J L, Hauser M A, Schmidt S, Scott W K, Olson L M, Gallins P, Spencer K L, Kwan S Y, Noureddine M, Gilbert J R, Schnetz-Boutaud N, Agarwal A, Postel E A, Pericak-Vance M A. Complement factor H variant increases the risk of age-related macular degeneration. Science. 2005 Apr. 15; 308(5720):419-21.
6. Clark S J, Higman V A, Mulloy B, Perkins S J, Lea S M, Sim R B, Day A J. His-384 allotypic variant of factor H associated with age-related macular degeneration has different heparin binding properties from the non-disease-associated form. J Biol Chem. 2006 Aug. 25; 281(34): 24713-20.
7. Harris C L, Lublin D M, Morgan B P. Efficient generation of monoclonal antibodies for specific protein domains using recombinant immunoglobulin fusion proteins: pitfalls and solutions. Journal of Immunological Methods, 2002, Vol 5.

The invention claimed is:

1. A method for determining a risk factor for a complement mediated disease in an individual comprising:
   a) obtaining a plasma sample from an individual to be tested;
   b) exposing said sample to at least one antibody, or antigen-binding fragment thereof, produced by a deposited hybridoma having an ECACC accession number A 07042601 (His402 variant) and specific for a histidine 402 variant (His402 variant) of Complement Factor H, and/or at least one antibody, or antigen-binding fragment thereof, produced by a deposited hybridoma having an ECACC accession number A 08011002 (Tyr402 variant) and specific for a tyrosine 402 variant (Tyr402 variant) of Complement Factor H;
   c) determining specific binding of said antibody to plasma Complement Factor H and where binding of the histidine specific antibody produced by the deposited hybridoma having the ECACC accession number A 07042601 takes place concluding that the histidine 402 variant is present, or where binding of the tyrosine specific antibody produced by the deposited hybridoma having the ECACC accession number A 08011002 takes place concluding that the tyrosine 402 variant is present; and
   d) where the histidine 402 variant is present, concluding that the individual either has, or is at increased risk of developing a complement mediated disease, or where the binding of only the tyrosine specific antibody indicates a homozygous state for the tyrosine 402 variant, i.e. that there is no histidine 402 variant present, concluding that the individual is at reduced risk of developing a complement mediated disease.

2. The method according to claim 1 wherein said antibody or antigen-binding fragment thereof is specific for the histidine 402 variant of Complement Factor H.

3. The method according to claim 1 wherein said antibody or antigen-binding fragment thereof is specific for the tyrosine 402 variant of Complement Factor H.

4. The method according to claim 1 wherein step b) includes exposing said sample to only the antibody or antigen-binding fragment thereof specific for the tyrosine 402 variant of Complement Factor H and step c) includes quantitatively determining whether the individual is homozygous for the tyrosine variant.

5. The method according to claim 1 wherein the disease is Age-Related Macular Degeneration.

6. The method according to claim 1 wherein following step b) unbound antibodies are removed so that a subsequent determination of binding can be undertaken without, or with a minimum amount of, background interference from unbound antibodies.

7. The method according to claim 1 wherein step a) is followed by a step of exposing plasma to antibody or antigen-binding fragment thereof that recognises both variants of Complement Factor H and washing away any unbound plasma proteins.

8. The method according to claim 7, further including adding a secondary antibody linked directly or indirectly to a labeling system, said secondary antibody binding an isoform-specific antibody or antigen-binding fragment thereof specific for one of the His402 variant or Tyr 402 variant.

9. The method according to claim 8 wherein said labelling system includes any one or more of the following: enzyme-linked immunosorbent assay (ELISA) systems, bioluminescent systems, chemiluminescent systems or pigmented indicator systems.

10. An isolated antibody or antigen-binding fragment thereof that is specific for a histidine 402 variant of Complement Factor H, said antibody being produced by a deposited hybridoma having an ECACC accession number A 07042601.

11. An isolated non-human clone that secretes the antibody according to claim 10.

12. An isolated antibody or antigen-binding fragment thereof that is specific for a tyrosine 402 variant of Complement Factor H, said antibody being produced by a deposited hybridoma having an ECACC accession number A 08011002.

13. An isolated non-human clone that secretes the antibody according to claim 12.

14. A therapeutic composition for inhibiting binding of Complement Factor H to either ligands or tissues, comprising a monoclonal antibody or antigen-binding fragment thereof, specific for either a histidine 402 variant or a tyrosine 402 variant of Complement Factor H, said monoclonal antibody being produced by a deposited hybridoma having an ECACC accession number A 07042601 (histidine 402 variant) or a deposited hybridoma having an ECACC accession number A 08011002 (tyrosine 402 variant).

15. A kit for determining a risk factor for a complement mediated disease in an individual according to the method set forth in claim 1, wherein said kit comprises an isolated antibody or antigen-binding fragment thereof, specific for the histidine 402 variant of Complement Factor H and/or an isolated antibody or antigen-binding fragment thereof, specific for the tyrosine 402 variant of Complement Factor H, said antibody being produced by the deposited hybridoma having an ECACC accession number A 07042601 (histidine 402 variant) or the deposited hybridoma having an ECACC accession number A 08011002 (tyrosine 402 variant); and an indicator or label for determining binding of said isolated antibody or antigen-binding fragment thereof to Complement Factor H.

16. The kit according to claim 15 wherein said kit further includes an isolated antibody, or antigen-binding fragment thereof, that recognises any isoform of Complement Factor H.

17. The kit according to claim 16 wherein said antibody or antigen-binding fragment thereof that recognizes any isoform of Complement Factor H is monoclonal or polyclonal.

18. The kit according to claim 15 wherein said kit further includes labelling means that enables binding of said one or more antibodies, or antigen-binding fragments thereof, to Complement Factor H to be determined.

19. The kit according to claim 18 wherein said kit includes a secondary antibody which is coupled to an enzyme-linked immunosorbent assay (ELISA) system or a light activated assay system or a pigmented assay system.

20. The kit according to claim 19 wherein said secondary antibody has an antigen-binding specificity for the antibody produced by the deposited hybridoma having an ECACC accession number A 07042601 (His 402 variant) or the deposited hybridoma having an ECACC accession number A 08011002 (Tyr402 variant).

* * * * *

UNITED STATES PATENT AND TRADEMARK OFFICE
CERTIFICATE OF CORRECTION

PATENT NO. : 8,501,427 B2
APPLICATION NO. : 12/524196
DATED : August 6, 2013
INVENTOR(S) : Bryan Paul Morgan, Claire Louise Harris and Svetlana Hakobyan It is certified that error appears in the above-identified patent and that said Letters Patent is hereby corrected as shown below:

Title Page, Item (75) Inventors should read: Bryan Paul Morgan, Cardiff (GB);
Claire Louise Harris, Cardiff (GB);
Svetlana Hakobyan, Cardiff (GB)

Signed and Sealed this
Fifth Day of November, 2013

Teresa Stanek Rea
*Deputy Director of the United States Patent and Trademark Office*

```
                       SEQUENCE LISTING

<160> NUMBER OF SEQ ID NOS: 9

<210> SEQ ID NO 1
<211> LENGTH: 32
<212> TYPE: DNA
<213> ORGANISM: Human

<400> SEQUENCE: 1
gcgtctagaa ccttgaaacc ttgtgattat cc                                32

<210> SEQ ID NO 2
<211> LENGTH: 30
<212> TYPE: DNA
<213> ORGANISM: Human

<400> SEQUENCE: 2
cagggatcca gatttaatgc acgtgggttg                                   30

<210> SEQ ID NO 3
<211> LENGTH: 21
<212> TYPE: DNA
<213> ORGANISM: Human

<400> SEQUENCE: 3
aatcaaaatt atggaagaaa g                                            21

<210> SEQ ID NO 4
<211> LENGTH: 21
<212> TYPE: DNA
<213> ORGANISM: Human

<400> SEQUENCE: 4
ctttcttcca taattttgat t                                            21

<210> SEQ ID NO 5
<211> LENGTH: 9
<212> TYPE: PRT
<213> ORGANISM: Human

<400> SEQUENCE: 5

Gly Gly Gly Gly Ser Gly Gly Gly Ser
1               5

<210> SEQ ID NO 6
<211> LENGTH: 11
<212> TYPE: PRT
<213> ORGANISM: Human
```

-continued

```
<400> SEQUENCE: 6

Tyr Leu Glu Asn Gly Tyr Asn Gln Asn Tyr Gly
1               5                   10

<210> SEQ ID NO 7
<211> LENGTH: 12
<212> TYPE: DNA
<213> ORGANISM: Human

<400> SEQUENCE: 7
aatcaaaatt at                                                              12

<210> SEQ ID NO 8
<211> LENGTH: 11
<212> TYPE: PRT
<213> ORGANISM: Human

<400> SEQUENCE: 8

Tyr Leu Glu Asn Gly Tyr Asn Gln Asn His Gly
1               5                   10

<210> SEQ ID NO 9
<211> LENGTH: 12
<212> TYPE: DNA
<213> ORGANISM: Human

<400> SEQUENCE: 9
aatcaaaatc at                                                              12
```